United States Patent [19]

Hector et al.

[11] Patent Number: 5,019,560
[45] Date of Patent: May 28, 1991

[54] METHOD FOR TREATING FUNGAL INFECTIONS WITH NIKKOMYCIN DERIVATIVES

[75] Inventors: Richard F. Hector, Dublin, Calif.; Klaus Schaller, Wuppertal; Heinrich F. Moeschler; Manfred Plempel, both of Leverkusen, all of Fed. Rep. of Germany

[73] Assignee: Bayer AG, Leverkusen, Fed. Rep. of Germany

[21] Appl. No.: 252,613

[22] Filed: Oct. 3, 1988

[51] Int. Cl.$^5$ .................. A61K 31/71; A61K 31/70
[52] U.S. Cl. ........................... 514/43; 514/23; 514/50; 536/23; 536/24
[58] Field of Search .............. 514/43, 50, 396, 23; 536/23, 24

[56] References Cited

U.S. PATENT DOCUMENTS

| | | | |
|---|---|---|---|
| 4,046,881 | 9/1977 | Dähn et al. | 424/181 |
| 4,158,608 | 6/1979 | Dähn et al. | 195/80 R |
| 4,287,186 | 9/1981 | Zähner et al. | 424/181 |
| 4,315,422 | 2/1982 | Hagenmaier et al. | 424/181 |
| 4,402,947 | 9/1983 | Moeschler et al. | 424/181 |
| 4,552,954 | 11/1985 | Moeschler et al. | 536/24 |
| 4,585,761 | 4/1986 | Zähner et al. | 514/43 |
| 4,851,389 | 7/1989 | Hector et al. | 514/43 |

OTHER PUBLICATIONS

The Merck Index, 10th Edition.
Lehninger (1975) Biochemistry, Worth Publishers, The Johns Hopkins University, p. 312.
Morrisson and Boyd 1983, *Organic Chemistry* Fourth Edition (Allyn and Bacon, Boston), pp. 565–566.

*Primary Examiner*—Johnnie R. Brown
*Assistant Examiner*—Gary L. Kunz
*Attorney, Agent, or Firm*—James A. Giblin

[57] ABSTRACT

A method of treating a mammal infected with a dimorphic, highly chitinous fungi, the method comprising administering to the mammal therapeutically effective amounts of a nikkomycin derivative having the following structure:

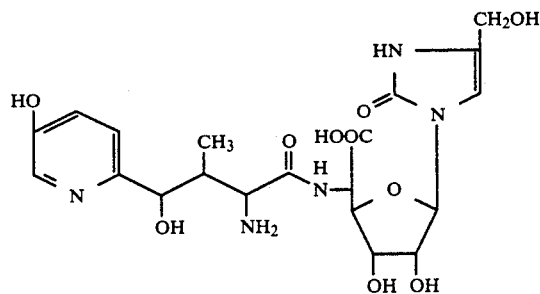

7 Claims, 1 Drawing Sheet

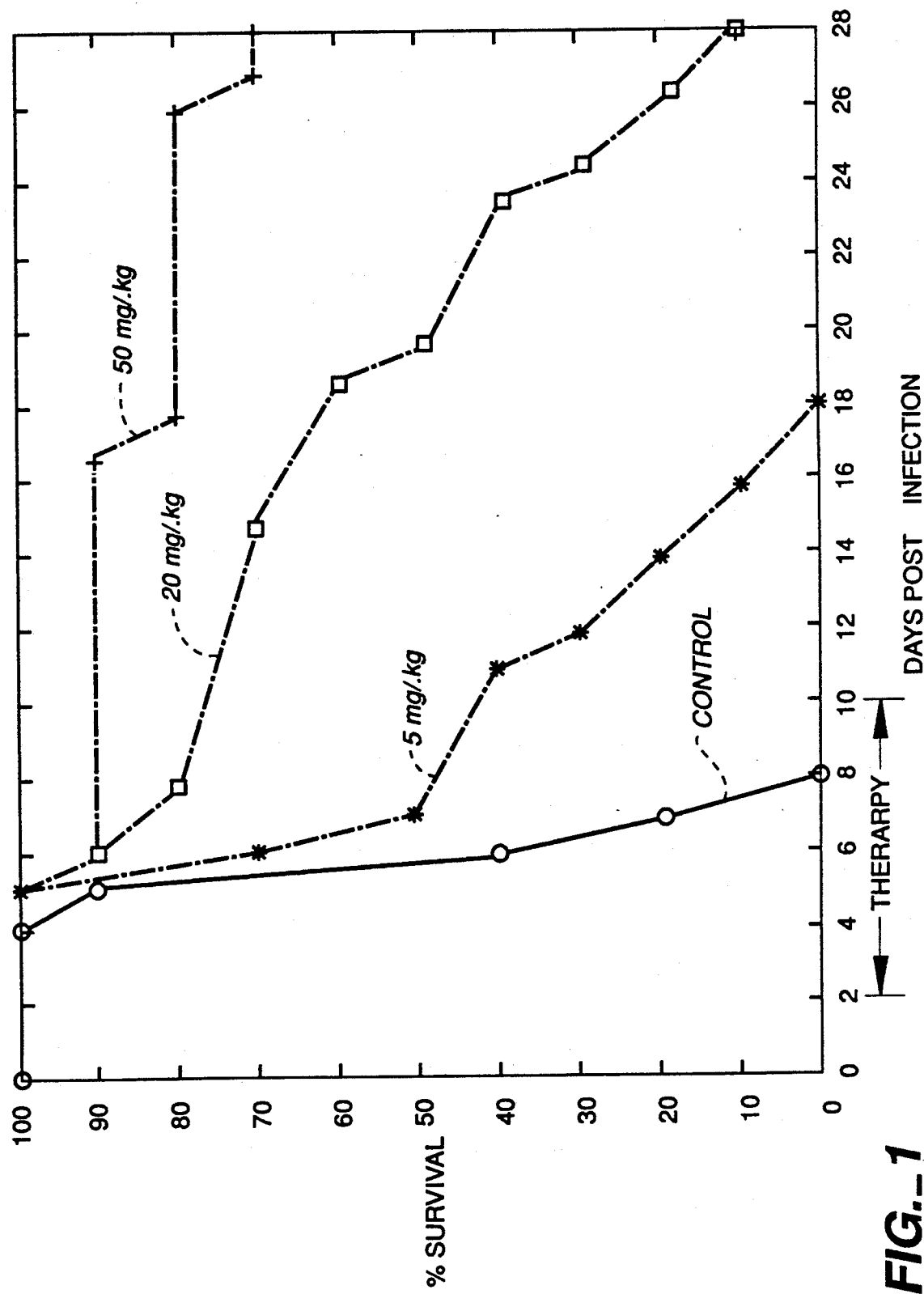
FIG._1

METHOD FOR TREATING FUNGAL INFECTIONS WITH NIKKOMYCIN DERIVATIVES

The invention is related to nikkomycin derivatives, antimycotic compositions containing nikkomycin derivatives, antimycotic compositions comprising fungicidally effective amounts of a nikkomycin derivative and an azole antimycotic, the preparation of such compositions and the methods of treating infections of fungi by administering therapeutically effective amounts of such compositions.

Compounds inhibitory to the synthesis of fungal cell wall material (synthetase inhibitors) have been reported recently to have demonstrable effects against fungi of agricultural importance (U.S. Pat. Nos. 4,315,922 and 4,158,608; see also U.S. Pat. Nos. 4,585,761 and 4,552,954 for descriptions of the preparation and purification of such compounds). The agents mentioned in the cited patents, nikkomycins, together with similar agents known as polyoxins, are know to act by interfering with the synthesis of chitin in the cell walls of fungi. Because fungi of medical importance to humans also have varying amounts of chitin in their cell walls, experiments have been conducted to determine if the chitin synthase inhibitors are capable of inhibiting the growth of such fungi (Hector and Pappagianis, J. Bacteriol. 154:488-498, 1983, and Hector and Braun, Antimicrobial Agents Chemother, 29:389-394, (1986). In earlier work, certain fungi such as *Candida albicans* were reported to be insensitive to chitin synthase inhibitors (see Naider et al, Antimicrobial Agents Chemother, 24:787-796, 1983). Subsequently, *C. albicans* was found to be more sensitive to nikkomycins than polyoxins (see Yadan et al, J. Bacteriol. 160:884-888, 1984).

Quite surprisingly, it was now found that nikkomycin derivatives in combination with antimycotically active azoles are efficacious in treating fungal infections in human and non-human animals, especially by parenteral but also oral application and administration.

As shown in synergy studies the achieved antifungal effect is also a synergistic effect based on combining the nikkomycin derivatives with antimycotic azoles.

Accordingly, the invention is related to new nikkomycin derivatives and antimycotic compositions comprising a fungicidally effective amount of a nikkomycin derivative and an azole antimycotic.

The nikkomycin derivatives of the invention are represented by the general formula (N)

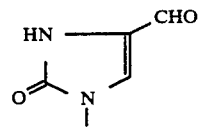

(N)

wherein
$R_n$ represents

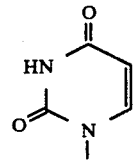

$R_w$ denotes H and
$R_y$ denotes a radical

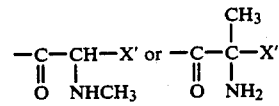

wherein X' is any saturated or unsaturated organic radical, expecially a radical derived from a natural amino acid, especially

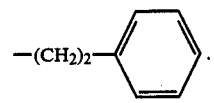

X' in formula (N) represents also alkyl, preferably $C_1$-$C_6$-alkyl, aryl, preferably $C_6$-$C_{18}$-aryl, aralkyl, preferably $C_6$-$C_{12}$-aryl-$C_1$-$C_6$-alkyl.

Moreover, the invention is related to Nikkomycin derivatives of the general formula (N')

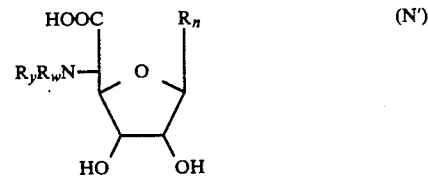

wherein $R_n$ represents

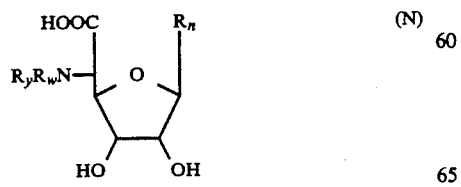

(a) $R_w$ denotes H or —$CH_2$—X, wherein X is H, alkyl, preferably $C_1$-$C_6$-alkyl, aryl, preferably $C_6$-$C_{18}$-aryl, aralkyl, preferably $C_6$-$C_{12}$-aryl-$C_1$-$C_6$-alkyl or any other saturated or unsaturated organic radical and $R_y$ denotes —$CH_2$—X, wherein X has the aforementioned meaning;

(b)
$R_w$ denotes H and
$R_y$ denotes

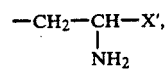

wherein X' is any saturated or unsaturated organic radical, especially a radical derived from a natural amino acid and derivatives of homophenylalanine;

(c)

$R_w$ denotes H and
$R_y$ denotes a radical

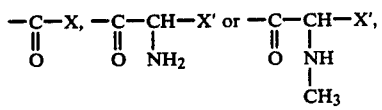

wherein X and X' have the meaning mentioned under (a) and (b) hereinbefore and X has additionally the meaning

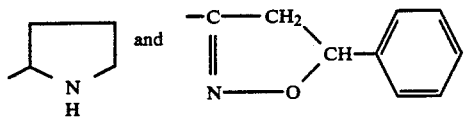

with the proviso that X' in the radical

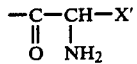

has not the meaning

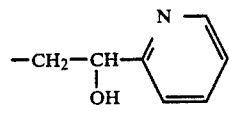

or

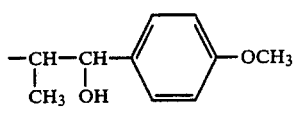

or

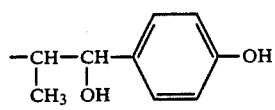

(d)
$R_w$ denotes H and
$R_y$ has the meaning of (a') $R_{n'}$ denotes H or $CH_2$—X and $R_{y'}$ denotes —$CH_2$—X, wherein X has the meaning mentioned under (a) hereinabove;

(b') $R_{n'}$ represents H and $R_{y'}$ means

—CH$_2$—CH—X'
         |
         NH$_2$ wherein X' has the meaning mentioned under (b) hereinbefore;

(c') $R_{n'}$ denotes H and $R_{y'}$ represents

—C—X
 ‖
 O and

—C—CH—X'
 ‖   |
 O   NH$_2$ wherein X and X' have the meaning given under (a) and (b) hereinabove.

(d') $R_{n'}$ denotes H and $R_{y'}$ represents

H
        |
—C—N—X,
 ‖
 O wherein X has the meaning given under (a) hereinabove and —CH$_3$, [phenyl], [chlorophenyl], [trifluoromethylphenyl], [methylchlorophenyl] or —CH$_2$—[phenyl].

or to Nikkomycin derivatives of the general formula (N")

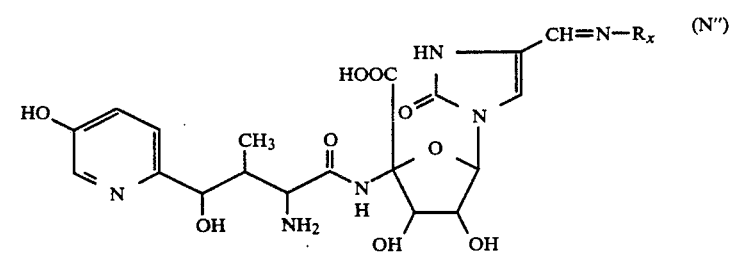

wherein $R_x$ denotes any organic radical including heterocycles especially a radical of the general formula —NH—$R_{x'}$, where $R_{x'}$ is alkyl, preferably $C_1$-$C_6$ alkyl, aryl, preferably $C_6$-$C_{18}$ aryl, a $C_6$-$C_{18}$ alkyl, phenyl, substituted phenyl or more preferably

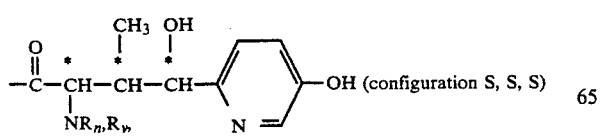

(configuration S, S, S)

wherein

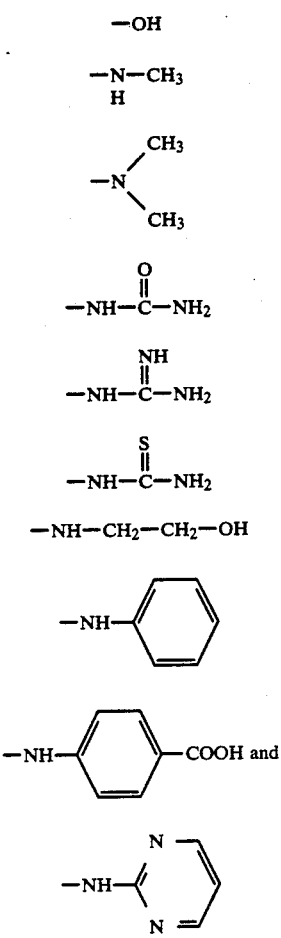

A preferred object of the present invention are antimycotic compositions containing the above identical Nikkomycin derivatives and azole antimycotics more specifically described in GB-PS 1,351,542, CA-PS 225,504, CA-AS 946,391, AU-PS 542,110, AU-PS 551,411, U.S. Pat. No. 4,301,166, U.S. Pat. No. 4,381,306, U.S. Pat. No. 4,246,274, U.S. Pat. No. 4,238,498, U.S. Pat. No. 4,207,328, U.S. Pat. No. 3,968,229 and DE-OS 3,242,249 which are incorporated into this patent application by reference.

Another preferred embodiment of the present invention are antimycotic compositions containing nikkomycin derivatives of the hereinbefore defined type and azole antimycotics described in the following paragraphs.

(a) Diazolylalkyl-carbinols of the general formula

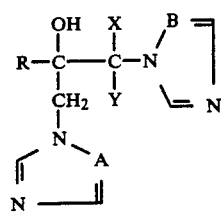

in which
A represents a nitrogen atom or the CH group,
B represents a nitrogen atom or the CH group,
X represents hydrogen or alkyl,
Y represents alkyl, or alkenyl, alkinyl or optionally substituted benzyl, if X represents hydrogen, and
R represents optionally substituted phenyl or the grouping

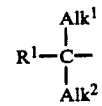

wherein
Alk$^1$ represents alkyl and
Alk$^2$ represents alkyl, or
Alk$^1$ and Alk$^2$ together represent a cycloaliphatic ring, and
R$^1$ represents alkyl, alkenyl or in each case optionally substituted phenyl, phenylalkyl, phenoxy, phenylthio, phenoxyalkyl, phenylthioalkyl, benzyloxy or benzylthio,
and physiologically acceptable acid addition salts thereof.

The compounds of the formula (I) sometimes have two asymmetric carbon atoms. In this case, they can exist in two geometric isomer forms.

The substituted diazolylalkyl-carbinols of the formula (I) are obtained by a process in which azolyloxiranes of the formula

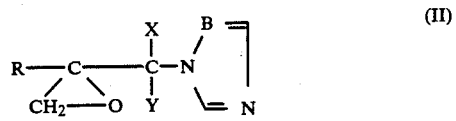

in which B, R, X and Y have the abovementioned meaning, are reacted with azoles of the formula

in which A has the abovementioned meaning, in the presence of a diluent and, if appropriate, in the presence of a base.

Preferably, in formula (I)
A represents a nitrogen atom or the CH group,
B represents a nitrogen atom or the CH group,
X represents hydrogen or straight-chain or branched alkyl with 1 to 6 carbon atoms,
Y represents straight-chain or branched alkyl with 1 to 6 carbon atoms; or, if X represents hydrogen, also straight-chain or branched alkenyl or alkinyl with in each case 3 to 6 carbon atoms or benzyl with is optionally mono-, di- or tri-substituted in the phenyl art by identical or different substituents, substituents which may be mentioned being: halogen, alkyl with 1 to 4 carbon atoms, alkoxy and alkylthio with in each case 1 to 4 carbon atoms, halogenoalkyl, halogenoalkoxy and halogenoalkylthio with in each case 1 or 2 carbon atoms and 1 to 5 identical or different halogen atoms, such as, preferably, flourine and chlorine atoms, nitro- and cyano; and
R represents phenyl which is optionally mono-, di-or tri-substituted by identical or different substituents, preferred substituents which may be mentioned being: halogen, alkyl with 1 to 4 carbon atoms, alkoxy and alkylthio with in each case 1 to 4 carbon atoms, halogenoalkyl, halogenoalkoxy and halogenoalkylthio with in each case 1 or 2 carbon atoms and 1 to 5 identical or different halogen atoms, such as, preferably, fluorine and chlorine atoms, nitro, cyano, hydroxyl, hydroxycarbonyl, alkoxycarbonyl with 1 to 4 carbon atoms in the alkyl part, hydroximinoalkyl with 1 to 4 carbon atoms, alkoximinoalkyl with 1 to 4 carbon atoms in each alkyl part and phenyl, phenoxy, benzyl and benzyloxy, each of which is optionally substituted by halogen and/or alkyl with 1 or 2 carbon atoms; or R preferably represents the grouping $$R^1-\underset{\underset{Alk^2}{|}}{\overset{\overset{Alk^1}{|}}{C}}-$$

wherein

Alk$^1$ represents straight-chain or branched alkyl with 1 to 4 carbon atoms; and Alk$^2$ represents straight-chain or branched alkyl with 1 to 4 carbon atoms; or Alk$^1$ and Alk$^2$, together with the carbon atom to which they are bonded, represent a 3-membered to 7-membered cycloaliphatic ring; and R$^1$ represents straight-chain or branched alkyl with 1 to 6 carbon atoms, alkenyl with 2 to 4 carbon atoms, or phenyl, phenylalkyl with 1 to 4 carbon atoms in the alkyl part, phenoxy, phenylthio, phenoxyalkyl with 1 to 4 carbon atoms in the alkyl part, phenyl, thioalkyl with 1 to 4 carbon atoms in the alkyl part, benzyloxy or benzylthio, each of which is optionally mono-, di- or tri-substituted in the phenyl part by identical or different substituents, preferred possible substituents being the substituents on phenyl already mentioned for R.

Particularly preferred compounds of the formula (I) are those in which

A represents a nitrogen atom or the CH group,

B represents a nitrogen atom or the CH group,

X represents hydrogen or straight-chain or branched alkyl with 1 to 4 carbon atoms, Y represents straight-chain or branched alkyl with 1 to 4 carbon atoms; or, if X represents hydrogen, also allyl, methallyl, propargyl, methylpropargyl or benzyl which is optionally mono- or di-substituted in the phenyl part by identical or different substituents, substituents which may be mentioned being: fluorine, chlorine, bromine, methyl, isopropyl, tert.-butyl, methoxy, methylthio, trifluoromethyl, trifluoromethoxy, trifluoromethylthio, nitro and cyano;

R represents phenyl which is optionally mono- or di-substituted by identical or different substituents, substituents which may be mentioned being: fluorine, chlorine, bromine, methyl, isopropyl, tert.-butyl, methoxy, methylthio, trifluoromethyl, trifluoromethoxy, trifluoromethylthio, nitro, cyano, hydroxyl, hydroxycarbonyl, methoxycarbonyl, ethoxycarbonyl, hydroximinomethyl, 1-hydroximinoethyl, methoximinomethyl, 1-methoximinoethyl and phenyl, phenoxy, benzyl and benzyloxy, each of which is optionally substituted by fluorine, chlorine or methyl; or R represents the grouping $$R^1-\underset{\underset{Alk^2}{|}}{\overset{\overset{Alk^1}{|}}{C}}-$$

wherein

Alk$^1$ represents methyl or ethyl; and

Alk$^2$ represents methyl or ethyl; or

Alk$^1$ and Alk$^2$, together with the carbon atom to which they are bonded, represent cyclobutyl, cyclopentyl or cyclohexyl; and R$^1$ represents methyl, ethyl, n-propyl, i-propyl, n-butyl, neopentyl, or phenyl, benzyl, phenethyl, phenoxy, phenylthio, phenoxymethyl, phenoxyethyl, phenylthiomethyl, phenylthioethyl, benzyloxy or benzylthio, each of which is optionally mono- or di-substituted in the phenyl part by identical or different substituents, possible substituents being the substituents on phenyl which have already been mentioned for R.

Addition products of acids and those substituted diazolylalkyl-carbinols of the formula (I) in which the substituents A, B, X, Y and R have the meanings which have already been mentioned as preferred for these substituents are also preferred compounds according to the invention.

Preferred acids which can be added on azoles mentioned under (a), (b), (c), (d) and (e) include hydrogen halide acids, such as, for example, hydrochloric acid and hydrobromic acid, in particular hydrochloric acid, and furthermore phosphoric acid, nitric acid, monofunctional and bifunctional carboxylic acids and hydroxycarboxylic acids, such as, for example acetic acid, maleic acid, succinic acid, fumaric acid, tartaric acid, citric acid, salicyclic acid, sorbic acid and lactic acid, and sulphonic acids, such as o-toluenesulphonic acid and 1,5-naphthalenedisulphonic acid.

(b) Substituted 1,3-diazolyl-2-propanols of the general formula $$R-\underset{\underset{Alk^2}{|}}{\overset{\overset{Alk^1}{|}}{C}}-\underset{\underset{CH_2}{|}}{\overset{\overset{OH}{|}}{C}}-\underset{\underset{Y}{|}}{\overset{\overset{X}{|}}{C}}-N\underset{N}{\overset{X}{\diagup}}\underset{\diagdown}{\diagup}\underset{N-}{\overset{}{\diagdown}}Y \qquad (I')$$

in which

Alk$^1$ represents straight-chain or branched alkyl and

Alk$^2$ represents straight-chain or branched alkyl, or

Alk$^1$ and Alk$^2$ together represent a cycloaliphatic ring,

X represents a nitrogen atom or the CH group,

Y represents a nitrogen atom or the CH group and

R represents in each case optionally substituted phenyl, phenylalkyl, phenoxy, phenylthio, phenoxyalkyl, phenylthioalkyl, benzyloxy or benzylthio, and physiologically acceptable acid addition salts thereof.

The substituted 1,3-diazolyl-2-propanols of the formula (I') are obtained by a process in which 2-azolylmethyl-oxiranes of the formula

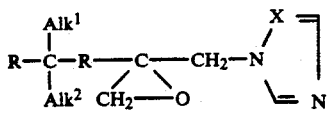 (II')

in which $Alk^1$, $Alk^2$, R and X have the abovementioned meaning, are reacted with azoles of the formula

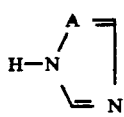 (III')

in which Y has the abovementioned meaning, in the presence of a diluent and, if appropriate, in the presence of a base.

If appropriate, an acid can then be added onto the compounds of the formula (I') thus obtained.

Moreover, the compounds of the general formula (I') in which R represents in each case optionally substituted phenylthio, phenylthioalkyl or benzylthio can be oxidised to the corresponding SO or $SO_2$ derivatives in the customary manner.

Formula (I') provides a general definition of substituted 1,3-diazolyl-2-propanols according to this section (b) of the invention. Preferably, in this formula, $Alk^1$ represents straight-chain or branched alkyl with 1 to 4 carbon atoms; and $Alk^2$ represents straight-chain or branched alkyl with 1 to 4 carbon atoms; or $Alk^1$ and $Alk^2$ together represent a 3-membered to 7-membered cycloaliphatic ring, X represents a nitrogen atom or the CH group;

Y represents a nitrogen atom or the CH group; and

R represents phenyl, phenylalkyl with 1 to 4 carbon atoms in the alkyl part, phenoxy, phenylthio, phenoxyalkyl with 1 to 4 carbon atoms in the alkyl part, phenylthioalkyl with 1 to 4 carbon atoms in the alkyl part, benzyloxy or benzylthio, each of which is optionally mono-, di- or tri-substituted in the phenyl part by identical or different substituents, preferred substituents which may be mentioned being: halogen, alkyl with 1 to 4 carbon atoms, alkoxy and alkylthio with in each case 1 to 4 carbon atoms, halogenoalkyl, halogenoalkoxy and halogenoalkylthio with in each case 1 or 2 carbon atoms and 1 to 5 identical or different halogen atoms, such as, preferably, fluorine and chlorine atoms, nitro, cyano, hydroxyl, hydroxycarbonyl, alkoxycarbonyl with 1 to 4 carbon atoms in the alkyl part, alkoximinoalkyl with 1 to 4 carbon atoms in each alkyl part, and phenyl, phenoxy, benzyl and benzyloxy, each of which is optionally substituted by halogen and/or alkyl with 1 or 2 carbon atoms.

Particularly preferred compounds of the formula (I') are those in which $Alk^1$ represents methyl or ethyl; and $Alk^2$ represents methyl or ethyl; or $Alk^1$ and $Alk^2$, together with the carbon atom to which they are bonded, represent cyclobutyl, cyclopentyl or cyclohexyl, X represents a nitrogen atom or the CH group;

Y represents a nitrogen atom or the CH group; and

R represents phenyl, benzyl, phenethyl, phenoxy, phenylthio, phenoxymethyl, phenoxyethyl, phenylthiomethyl, phenylthioethyl, benzyloxy or benzylthio, each of which is optionally mono- or disubstituted in the phenyl part by identical or different substituents, substituents which may be mentioned being: fluorine, chlorine, bromine, methyl, isopropyl, tert.-butyl, methoxy, methylthio, trifluoromethyl, trifluoromethoxy, trifluoromethylthio, nitro, cyano, hydroxyl, hydroxycarbonyl, methoxycarbonyl, ethoxycarbonyl, hydroximinoethyl, 1-hydroximinoethyl, methoximinomethyl, 1-methoximinoethyl, and phenyl, phenoxy, benzyl and benzyloxy, each of which is optionally substituted by fluorine, chlorine or methyl.

Addition products of acids and those substituted 1,3-diazolyl-2-propanols of the formula (I') in which the substituents $Alk^1$, $Alk^2$, X, Y and R have the meanings which have already been mentioned as preferred for these substituents are also preferred compounds according to the invention.

(c) Substituted azolylcyclopropyl-azolylmethyl-carbinol derivatives of the formula (I'')

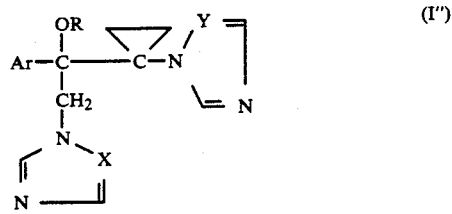 (I'')

in which

Ar represents optionally substituted aryl or optionally substituted heteroaryl,

R represents hydrogen, alkyl, alkenyl, alkinyl, trialkylsilyl, optionally substituted phenylalkyl or the acyl radical, X represents a nitrogen atom or the CH group, and Y represents a nitrogen atom or the CH group, and their acid addition salts have good anitimicrobial, in particular antimycotic, properties when used according to this invention.

The substituted azolylcyclopropyl-azolylmethyl-carbinol derivatives of the formula (I'') which are to be used according to the invention show a good spectrum of action in certain areas of indication.

The substituted azolylcyclopropyl-azolylmethyl-carbinol derivatives are generally defined by formula (I''). In this formula, Ar preferably represents phenyl which optionally has one or several, identical or different, substituents, the substituents which may be mentioned as being preferred being: halogen; alkyl, alkoxy and alkylthio each having 1 to 4 carbon atoms; halogenoalkyl, halogenoalkoxy and halogenoalkylthio each having 1 to 2 carbon atoms and 1 to 5 identical or different halogen atoms, such as fluorine and chlorine atoms; as well as phenyl or phenoxy each of which is optionally substituted by alkyl having 1 or 2 carbon atoms and/or halogen; and furthermore represents naphthyl and a 5- to 6-membered heteroaromatic which optionally has one or several identical or different, substituents and nitrogen, oxygen and/or sulphur as the heteroatoms, the suitable substituents which are preferred being the abovementioned phenyl substituents;

R preferably represents hydrogen, straight-chain or branched alkyl having 1 to 4 carbon atoms, straight-chain or branched alkenyl and alkinyl each having 2 to 4 carbon atoms, trialkylsilyl having 1 to 4 carbon atoms in each alkyl moiety, alkylcarbonyl having 1 to 4 carbon atoms in the alkyl moiety, and represents phenylalkyl which optionally has one or several, identical or different, substituents, with 1 to 2 carbon atoms in the alkyl moiety, the suitable substituents which are preferring being the phenyl substituents already mentioned for Ar; and X and Y represent the meanings given in the definition of the invention.

Particularly preferred compounds of the formula (I″) are those in which

Ar represents phenyl which optionally has one to three, in particular one or two, identical or different substituents, the substituents which may be mentioned being: fluorine, chlorine, methyl, isopropyl, tert.-butyl, methoxy, methylthio, trifluoromethyl, trifluoromethoxy, trifluoromethylthio, and phenyl or phenoxy each of which is optionally substituted by fluorine, chlorine and/or methyl; furthermore represents naphthyl and represents furyl, thienyl, pyridinyl or pyrimidinyl, each of which optionally has one or two, identical or different, substituents suitable substituents being the abovementioned phenyl substituents;

$R^1$ represents hydrogen, methyl, ethyl, n-propyl, isopropyl, n-butyl, isobutyl, allyl, propargyl, trimethylsilyl, methylcarbonyl, ethylcarbonyl, n-propylcarbonyl, isopropylcarbonyl, n-butylcarbonyl, isobutylcarbonyl, and represents benzyl which optionally has one to three, in particular one or two, identical or different substituents, suitable substituents which are preferred being the phenyl substituents already mentioned for Ar; and X and Y represent the meanings given in the definition of the invention.

Preferred compounds according to this section of the invention are also addition products of acids and those substituted azolylcyclopropyl-azolylmethylcarbinol derivatives of the formula (I″) in which Ar, R, X and Y have the meanings which have already been mentioned as preferred for these radicals.

(d) Substituted azolylmethyl-cyclopropyl-carbinol derivatives of the formula (I‴)

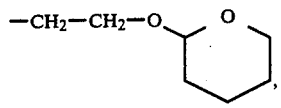

(I‴)

in which

Ar represents optionally substituted aryl or optionally substituted heteroaryl, $R^1$ represents hydrogen, alkyl, alkenyl, alkinyl, trialkylsilyl, optionally substituted phenylalkyl or the acyl radical, $R^2$ represents halogen, cyano, thiocyano, alkylcarbonyloxy, alkylcarbonylthio or the groups —X—$R^3$ and —N$R^4R^5$, as well as hydrogen when Ar represents optionally substituted heteroaryl, $R^3$ represents alkyl, cycloalkyl, alkenyl, alkinyl, hydroxyalkyl, carboxyalkyl, alkoxycarbonylalkyl, optionally substituted aryl, optionally substituted aralkyl, or the radical of the formula

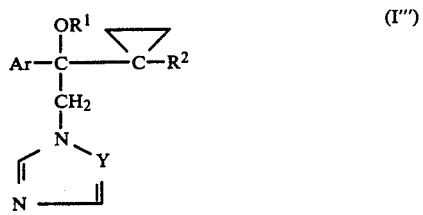

$R^4$ and $R^5$ are identical or different and represent hydrogen or alkyl and, together with the nitrogen atom to which they are bonded, represent an optionally substituted cycloaliphatic ring which optionally contains other heteroatoms, X represents oxygen, sulphur, the SO or $SO_2$ group, and Y represents a nitrogen atom or the CH group, and their acid addition salts, have good antimycotic properties.

The substituted azolylmethyl-cyclopropyl-carbinol derivatives of the formula (I‴) which are to be used according to this section of invention show a good spectrum of action in certain areas of indication.

The substituted azolylmethyl-cyclopropyl-carbinol derivatives according to the invention are generally defined by formula (I‴). In this formula, Ar preferably represents phenyl which optionally has one or several, identical or different, substituents, the substituents which may be mentioned as being preferred being: halogen, alkyl, alkoxy and alkylthio each having 1 to 4 carbon atoms; halogenoalkyl, halogenoalkoxy and halogenoalkylthio each having 1 to 2 carbon atoms and 1 to 5 identical or different halogen atoms, such as fluorine and chlorine atoms; as well as phenyl or phenoxy each of which is optionally substituted by alkyl having 1 or 2 carbon atoms and/or halogen; and furthermore represents naphthyl and a 5- to 6-membered heteroaromatic which optionally has one several, identical or different, substituents and nitrogen, oxygen and/or sulphur as the heteroatoms, the suitable substituents which are preferred being the above mentioned phenyl substituents;

$R^1$ preferably represents hydrogen, straight-chain or branched alkyl having 1 to 4 carbon atoms, straight-chain or branched alkenyl and alkinyl, each having 2 to 4 carbon atoms, trialkylsilyl having 1 to 4 carbon atoms in each alkyl part, alkylcarbonyl having 1 to 4 carbon atoms in the alkyl part, and phenylalkyl which has one or two carbon atoms in the alkyl part and is optionally monosubstituted or polysubstituted by identical or different substituents, preferred substituents being the phenyl substituents already mentioned for Ar, $R^2$ preferably represents fluorine, chlorine, bromine, cyano, thiocyano, alkylcarbonyloxy having 1 to 4 carbon atoms in the alkyl part, alkylcarbonylthio having 1 to 4 carbon atoms in the alkyl part, or the groupings —X—$R^3$ and —N$R^4R^5$, wherein
- R³ preferably represents straight-chain or branched alkyl having 1 to 18 carbon atoms, cycloalkyl having 3 to 8 carbon atoms, straight-chain or branched alkenyl having 2 to 18 carbon atoms, straight-chain or branched alkinyl having 2 to 18 carbon atoms, hydroxyalkyl having 1 to 18 carbon atoms, alkylthioalkyl having 1 to 6 carbon atoms in the alkylthio part and 1 to 6 carbon atoms in the alkyl part, carboxyalkyl having 1 to 18 carbon atoms in the alkyl part, alkoxycarbonylalkyl having 1 to 6 carbon atoms in the alkoxy part and 1 to 6 carbon atoms in the alkyl part, and phenyl or phenylalkyl having 1 to 2 carbon atoms in the alkyl part, each of which is optionally monosubstituted or polysubstituted by identical or different substituents, preferred substituents in each case being the phenyl substituents mentioned as being preferred for Ar, or
- R³ represents the radical of the formula

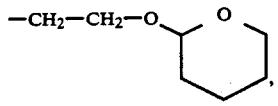

- R⁴ and R⁵ independently or one another preferably represent hydrogen or straight-chain or branched alkyl having 1 to 4 carbon atoms, or
- R⁴ and R⁵, together with the nitrogen atom to which they are bonded, preferably represent a 5-membered or 6-membered ring which is optionally substituted by alkyl having 1 to 4 carbon atoms or alkylcarbonyl having 1 to 4 carbon atoms in the alkyl part, and can contain oxygen, sulphur and/or nitrogen as further heteroatoms, and
- X preferably represents hydrogen when Ar represents an optionally substituted 5-membered or 6-membered heteroaromatic, and
- Y preferably represents nitrogen or a CH group.

Particularly preferred compounds of the formula (I''') are those in which
- Ar represents phenyl which is optionally monosubstituted or trisubstituted, in particular monosubstituted or disubstituted, by identical or different substituents, the following being mentioned as substituents: fluorine, chlorine, methyl, isopropyl, tert.-butyl, methoxy, methylthio, trifluoromethyl, trifluoromethoxy, trifluoromethylthio, and phenyl or phenoxy, each of which is optionally substituted by fluorine, chlorine and/or methyl; and furthermore represents naphthyl, and represents furyl, thienyl, pyridinyl or pyrimidinyl, each of which is optionally monosubstituted or disubstituted by identical or different substituents, suitable substituents being the above mentioned phenyl substituents;
- R² represents hydrogen, methyl, ethyl, n-propyl, isopropyl, n-butyl, isobutyl, allyl, propargyl, trimethylsilyl, methylcarbonyl, ethylcarbonyl, n-propylcarbonyl, isopropylcarbonyl, n-butylcarbonyl, isobutylcarbonyl, and benzyl which is optionally monosubstituted or disubstituted, in particular monosubstituted or disubstituted, by identical or different substituents, preferred substituents being the phenyl substituents already mentioned as being preferred for Ar,
- R² represents fluorine, chlorine, bromine, cyano, thiocyano, methylcarbonyloxy, ethylcarbonyloxy, n-propylcarbonyloxy, isopropylcarbonyloxy, n-butylcarbonyloxy, isobutylcarbonyloxy, methylcarbonylthio, ethylcarbonylthio, n-propylcarbonylthio, isopropylcarbonylthio, n-butylcarbonylthio, isobutylcarbonylthio or the groupings —X—R³ or —NR⁴R⁵, wherein
- R³ represents straight-chain or branched alkyl having 1 to 12 carbon atoms, cycloalkyl having 5 to 7 carbon atoms, straight-chain or branched alkenyl having 2 to 12 carbon atoms, straight-chain or branched alkinyl having 2 to 12 carbon atoms, hydroxyalkyl having 1 to 12 carbon atoms, alkylthioalkyl having 1 to 4 carbon atoms in the alkylthio part and 1 to 4 carbon atoms in the alkyl part; carboxyalkyl having 1 to 12 carbon atoms in the alkyl part, alkoxycarbonylalkyl having 1 to 4 carbon atoms in the alkoxy part and 1 to 4 carbon atoms in the alkyl part, and phenyl or benzyl, each of which is optionally monosubstituted to trisubstituted, in particular monosubstituted to trisubstituted, in particular monosubstituted or disubstituted, by identical or different substituents already mentioned above for Ar as being particularly preferred, or
- R³ represents the radical of the formula

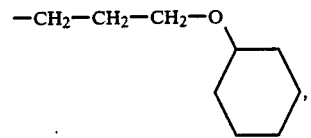

- R⁴ and R⁵ independently of one another represent hydrogen, methyl, ethyl, n-propyl, isopropyl, n-butyl or isobutyl, or
- R⁴ and R⁵ together with the nitrogen atom to which they are bonded, represent piperidinyl, piperazinyl or morpholinyl each of which is optionally substituted by methyl, ethyl, methylcarbonyl or ethylcarbonyl, and
- X represents oxygen, sulphur, an SO group or an SO₂ group, and furthermore
- R² also represents hydrogen when Ar represents one of the abovementioned optionally substituted heteroaromatics, and
- Y represents nitrogen or a CH group, other preferred compounds according to the invention are addition products of acids and those substituted azolylmethyl-cyclopropyl-carbinol derivatives of the formula (I''') in which Ar, R¹, R² and Y have the meanings which have already been mentioned as being preferred for these radicals.

The substituted azolylmethyl-cyclopropyl-carbinol derivatives which are to be used according to this section of the invention and their acid addition salts have not yet been described. They can be obtained in a generally known manner.

(e) Hydroxyethyl-azole derivatives of the general formula

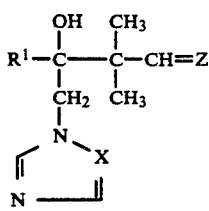 (I'''')

in which
R¹ represents alkyl or the grouping Ar—Y—,
Ar represents optionally substituted aryl,
Y represents a direct bond or the groupings —CH₂—, —CH₂—CH₂—, —OCH₂—, —SCH₂—, —CH=CH— or —C≡C—,
X represents a nitrogen atom or the CH group,
Z represents oxygen or the NOR² group and
R² represents hydrogen, alkyl, alkenyl, alkinyl, optionally substituted aralkyl or optionally substituted cycloalkylalkyl,
and acid addition salts thereof, have good antimycotic properties for the purpose of the present invention.

The compounds of the formula (I'''') have an asymmetric carbon atom and can therefore be obtained in the two optical isomer forms.

The hydroxyethyl-azole derivatives of the formula (I'''') to be used according to this section of the invention have a good action spectrum in certain fields of indication.

Formula (I'''') provides a general definition of the hydroxyethyl-azole derivatives according to the invention. Preferably, in this formula
R¹ represents straight-chain or branched alkyl with 1 to 6 carbon atoms or the grouping Ar—Y;
Ar represents naphthyl, or phenyl which is optionally monosubstituted or polysubstituted by identical or different substituents, preferred substituents which may be mentioned being: halogen, alkyl with 1 to 4 carbon atoms, alkoxy and alkylthio with in each case 1 or 2 carbon atoms, nitro, halogenoalkyl, halogenoalkoxy and halogenoalkylthio with in each case 1 or 2 carbon atoms and 1 to 5 identical or different halogen atoms, such as, preferably, fluorine and chlorine atoms, the —CH=NOR² radical, and phenyl, phenoxy, benzyl and benzyloxy, each of which is optionally substituted by halogen and/or alkyl with 1 or 2 carbon atoms;
X represents a nitrogen atom or the CH group;
Y represents a direct bond or the groupings —CH₂—, —CH₂CH₂—, —OCH₂—, —SCH₂—, —CH=CH— or —C≡C—;
Z represents oxygen or the NOR² group; and
R² represents hydrogen, straight-chain or branched alkyl with 1 to 6 carbon atoms, alkenyl or alkinyl with in each case 2 to 6 carbon atoms, or phenylalkyl which has 1 or 2 carbon atoms in the alkyl part and is optionally monosubstituted or polysubstituted by identical or different substituents, possible substituents on the phenyl being the substituents on phenyl which have already been mentioned in the case of Ar; or represents cycloalkylmethyl which has 5 or 6 carbon atoms in the cycloalkyl part and is optionally mono-, di- or trisubstituted by identical or different alkyl radicals with 1 to 3 carbon atoms.

Particularly preferred compounds of the formula (I'''') are those in which
R¹ represents straight-chain alkyl with 1 to 6 carbon atoms or the grouping Ar—Y—;
Ar represents naphthyl, or represents phenyl which is optionally mono-, di- or trisubstituted by identical or different substituents, substituents which may be mentioned being: fluorine, chlorine, methyl, trifluoromethyl, trifluoromethoxy, trifluoromethylthio, methoximinomethyl, ethoximinomethyl and alkyloximinomethyl, and phenyl, phenoxy, benzyl and benzyloxy, each of which is optionally substituted by chlorine and/or methyl;
X represents a nitrogen atom or the CH group;
Y represents a direct bond or the groupings —CH₂—, —CH₂CH₂—, —OCH₂—, —SCH₂—, —CH=CH— or —C≡C—; and
Z represents oxygen or the NOR² group,
wherein R² represents hydrogen, methyl, ethyl, n-propyl, n-butyl, allyl or propargyl, or represents benzyl which is optionally mono-, di- or trisubstituted by identical or different substituents from the group comprising fluorine, chlorine, methyl, trifluoromethyl and trifluoromethoxy, or represents cyclohexylmethyl which is optionally substituted by methyl or ethyl.

Another preferred embodiment of the invention are compositions comprising a fungicidally effective amount of a nikkomycin derivative selected from the group consisting of the nikkomycin derivatives identified above and optionally an antimycotically active and optionally orally applicable azole.

Moreover, antimycotic compositions are preferred comprising an azole antimycotic selected from the group consisting of ketoconazole, itraconazole, fluconazole, clotrimazole, miconazole, bifonazole, 1-(4-chlorphenyl)-2-methyl-2-methoximo-methyl-1-(1,2,4-triazol-1-yl-methyl)-1-propanol, 1-(4-chlorphenyl)-3,3-dimethyl-2-(1,2,4-triazol-1-yl-methyl)-2-butanol and 4-(fluorphenyl)-(1-methylsulfinyl-1-cyclopropyl)-(1,2,4-triazol-1-yl-methyl)-methanol.

The antimycotic compositions according to the invention contain a fungicidally effective amount of a nikkomycin derivative and an azole antimycotic in a ratio of 1:1 to 30:1, preferably 3:1 to 10:1.

Preferred are also antimycotic compositions according to the invention comprising a fungicidally effective amount of a nikkomycin derivative and identified above and an azole antimycotic selected from the group consisting of ketoconazole, itraconazole, fluconazole, clotrimazole, miconazole, bifonazole, 1-(4-chlorphenyl)-2-methyl-2-methoximo-methyl-1-(1,2,4-triazol-1-yl-methyl-1-propanol, 1-(4-chlorphenyl)-3,3-dimethyl-2-(1,2,4-triazol-1-yl-methyl)-2-butanol and 4-(fluorphenyl)-(1-methylsulfinyl-1-cyclopropyl)-(1,2,4-triazol-1-yl-methyl)-methanol and, moreover, the antimycotic compositions comprising a fungicidally effective amount of nikkomycin Z and 1(4-chlorphenyl)-2-methyl-2-methoximo-methyl 1-(1,2,3-triazol-1-yl-methyl-1-propanol, 1-(4-chlorphenyl)-3,3-dimethyl-2-(1,2,4-triazol-1-yl-methyl)-2-butanol and/or 4-(fluorphenyl)-(1-methylsulfinyl-1-cyclopropyl)-(1,2,4-triazol-1-yl-methyl)-methanol.

A further embodiment of the invention are nikkomycin derivatives as identified hereinbefore in combination with antimycotically active and optionally orally applicable azoles for use in a method for therapeutical treatment of the human or animal body infected with fungi.

The invention is also related to the use of nikkomycin derivatives as herein identified in combination with antimycotically active and optionally orally applicable azoles for the preparation of antimycotically active pharmaceutical compositions and to a process for the preparation of antimycotically active pharmaceutical compositions comprising mixing a combination of a fungicidally effective amount of a nikkomycin derivative and an azole derivative with a solid or liquid diluent and/or carrier or other auxiliaries useful for the preparation of pharmaceutical compositions, said nikkomycin derivative and azole derivative preferably being present in a ratio of 1:1 to 30:1, more preferred in a ratio of 3:1 to 10:1.

Finally, the invention is also related to a method of treating human or non-human animals infected with fungi, the method comprising administering to the human or non-human animal therapeutically effective amounts of a nikkomycin derivative and an azole antimycotic.

More specifically the invention is related to a method comprising administering to the human or nonhuman animal of from 1 mg/kg to 1000 mg/kg, preferably 10 mg/kg to 100 mg/kg of body weight per day of a nikkomycin derivative and an azole antimycotic of the above identified type. The method comprising administering the nikkomycin and the azole in a ratio of 1:1 to 30:1 preferred 3:1 to 10:1, is also preferred.

Preferably the compositions according to the invention are orally administered, but may be administered parenterally or via the inhalation of an aerosilized preparation.

EXPERIMENTAL PART FOR NIKKOMYCIN DERIVATIVES AND ANALOGUES

N-alkylation of nikkomycin X with aldehydes and ketones (Table 1, general procedure)

10 mmol of nikkomycin X are dissolved in 100 ml of an $H_2O$/methanol mixture and 50-100 mmol of the aldehyde or ketone dissolved in 20 ml of methanol are added. After stirring for 30 min. 10-15 mmol of $NaBH_3CN$ are added to the reaction mixture.

The mixture is stirred overnight (TLC control) until the reaction is complete. The excess $NaBH_3CN$ is eliminated by adding glacial acetic acid. The mixture is concentrated to dryness by evaporation and triturated with ether. The powdery product is chromatographed on LH-20 (ethanol/$H_2O$=1:1). In many cases the mono- and dialkylation products are produced concomitantly in the reaction with aldehydes. They are separated from each other by chromatography.

Derivatisation of the formyl group of nikkomycin X (Table 2, general procedure)

10 mmol of nikkomycin X (4.95 g) are suspended in 40 ml of an $H_2O$/methanol mixture and 15 mM of the hydrazine dissolved in 20 ml methanol are added. The pH is kept at 5.5 by adding a solution of Na-acetate (50% w/v).

The reaction mixture is stirred at room temperature. TLC control on cellulose using n-propanol/$H_2O$/acetic acid =60:40:0.5). The mixture is concentrated to dryness by evaporation and titurated with ether/THF.

The product is chromatographed on cellulose (n-propanol/$H_2O$/acetic acid =70/30/0.5).
Identification: 'H-NMR.

Derivatisation of nikkomycin X with isocyanates (table 3, general procedure)

10 mmol of nikkomycin X (4.95 g) are dissolved in 75 ml DMF and 10 mM of the isocyanate are added. The reaction mixture is stirred at room temperature. TLC control on cellulose using n-propanol/$H_2O$/acetic acid=70/30/0.5. If necessary, further 2 mM of the isocyanate are added.

The product is chromatographed on a modified styrene/DVB resin using a $H_2O$/methanol gradient.
Identification: 'H-NMR.

N-acylation of nikkomycin X with α-amino acid reactive esters (Table 4)

L-alanine-nikkomycin X 0.1 mmol nikkomycin X are dissolved in 1.2 ml of a DMF/$H_2O$ mixture (2:1) and 20 μl of triethylamine are added while cooling with ice. Then 0.11 mmol (33 mg) of N-BOC-L-alanine ONP-ester in 0.5 ml DMF and 13.5 mg of hydroxybenztriazole are added. TLC control on cellulose using n-propanol/$H_2O$/acetic acid=60:40:0.5 or 80:20:0.5.

The mixture is stirred overnight. After the reaction is complete the DMF/$H_2O$ mixture is stripped off under a high vacuum and the sample is dried (under a high vacuum). It is taken up in water and extracted first with ether and then with ethyl acetate in order to substantially remove residual DMF, hydroxybenztriazole and nitrophenol (pH kept at between 6–7). Then the aqueous phase is concentrated by evaporation and dried under a high vacuum.

To cleave the BOC protecting group from the tripeptide the product is dissolved in $CH_2Cl_2$/TFA=1:1 while cooling with ice and the solution is allowed to reach room temperature (TLC control). When the cleavage is complete the mixture is concentrated by evaporation, the remaining TFA is removed azeotropically with toluene and the product is dried under a high vacuum.

The product is chromatographed on LH-20 with ethanol/$H_2O$/acetic acid=50:50:0.1 (twice). 20 mg of an $^1$H-NMR-pure tripeptide are obtained.
Identification: $^1$H-NMR.

N-acylation of nikkomycin $C_x$ with α-amino acid reactive esters (table 5, example)

Homophenylalanine Nikkomycin X 0.5 mmols of $C_x$ (143.5 mg $C_x$) are dissolved in 6 ml of a DMF/$H_2O$ mixture (2:1) and 70 μl of triethylamine are added while cooling with ice. Then 0.55 mmols (44 mg) of N-BOC-homophenylalanine ONP-ester in 6 ml DMF are added.

Partially precipitated components dissolve on stirring the mixture overnight.

TLC control on cellulose using n-propanol/$H_2O$/acetic acid=60:40:0.5 or 80:20:0.5.

When the reaction is complete (pH kept at between 6–7) the DMF/$H_2O$ mixture is stripped off and the sample dried under a high vacuum. The product is worked up and TFA cleaved off following the same procedure as for the N-acylation of nikkomycin X with α-amino acid reactive esters.

The product is chromatographed on LH-20 using ethanol/$H_2O$/acetic acid=50:50:0.1.
Yield: 0.125 g (=55% total yield).
Identification: 'H-NMR.

N-acylation of nikkomycin $C_Z$ with α-amino reactive esters (table 7)

N-methylhomophenylalanine nikkomycin Z 0.5 mmol of $C_Z$ (143.5 mg) are dissolved in 4 ml DMF/$H_2O$ (2:1) and 70 μl of triethylamine are added while cooling with ice. Then 0.55 mmol of N-methyl L-homophenylalanine ONP-esters in 5 ml DMF are added.

Partially precipitated components dissolve on stirring the mixture overnight.

TLC control on cellulose using n-propanol/$H_2O$/acetic acid = 60:40:0.5 or 80:20:0.5.

When the reaction is complete (pH kept at between 6–7) the DMF/$H_2O$ mixture is stripped off and the sample dried under a high vacuum. The product is worked up and TFA cleaved off following the same procedure as for the N-acylation of nikkomycin X with α-amino acid reactive esters.

The product is chromatographed on LH-20 using $H_2O$/acetic acid = 99.9/0.1.

The yield was 35%.

Identification: $^1$H-NMR.

N-Methylnikkomycin Z 1 mmol of N-benzylnikkomycin Z prepared by reductive alkylation with benzaldehyde/NaBH$_3$CN is catalytically hydrogenated with 100 mg of platinum oxide in 100 ml of MeOH with the addition of 5 ml of formalin.

The solvent is removed under a high vacuum.

1.6 mM of N-methyl-N-benzylnikkomycin Z are hydrogenated with 1 g of palladium black in 25 ml of methanol and 50 μl of acetic acid. The catalyst is filtered off and the solvent stripped off.

The α-amino group of N-methylnikkomycin is partially (30%) racemised.

Identification: $^1$H-NMR.

TABLE 1

N-alkylation of nikkomycin X with aldehydes and ketones

| $R_1$ | $R_2$ | Physical Data |
|---|---|---|
| —CH$_3$ | —CH$_3$ | Structure confirmed by $^1$H-NMR data |
| —C$_2$H$_5$ | —C$_2$H$_5$ | |
| —C$_3$H$_7$ | —C$_3$H$_7$ | |
| -isoC$_3$H$_7$ | —H | |
| —C$_4$H$_9$ | —C$_4$H$_9$ | |
| —C$_7$H$_{15}$ | —H | |
| —C$_7$H$_{15}$ | —C$_7$H$_{15}$ | |
| —CH$_2$—CH=CH—CH$_3$ | —H | |
| —C$_2$H$_4$—OH | —H | |
| —CH(CH$_3$)(CH$_2$—CH$_2$—OH) | —H | |
| —CH$_2$—C$_6$H$_5$ | —H | Structure confirmed by $^1$H-NMR data |
| —CH$_2$—(2-hydroxyphenyl) | —H | |
| —CH$_2$—(4-hydroxyphenyl) | —H | |

TABLE 1-continued

N-alkylation of nikkomycin X with aldehydes and ketones

[Structure of nikkomycin X derivative shown with R$_1$ and R$_2$ substituents on the nitrogen]

| R$_1$ | R$_2$ | Physical Data |
|---|---|---|
| —CH$_2$—C$_6$H$_4$—OH (4-) | —H | |
| —CH$_2$—C$_6$H$_4$—NO$_2$ (4-) | —H | |
| —CH$_2$—C$_6$H$_4$—F (2-) | —H | |
| —CH$_2$—C$_6$H$_4$—F (3-) | —H | |
| —CH$_2$—C$_6$H$_3$—F$_2$ (2,4-) | —H | |
| —CH$_2$—C$_6$F$_5$ | —H | Structure confirmed by $^1$H-NMR data |
| —CH$_2$—C$_6$H$_4$—Cl (4-) | —H | |
| —CH$_2$—C$_6$H$_2$Cl$_2$(OH) (3,5-diCl-4-OH) | —H | |
| —CH$_2$—C$_6$H$_4$—CH$_3$ (4-) | —H | |

TABLE 1-continued
N-alkylation of nikkomycin X with aldehydes and ketones
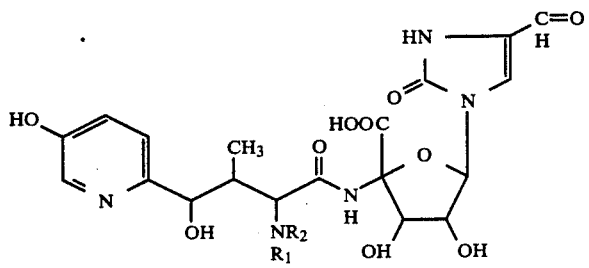
| $R_1$ | $R_2$ | Physical Data |
|---|---|---|
| -CH₂-C₆H₄-OCH₃ (p) | -H | |
| -CH₂-C₆H₃(OH)(OCH₃) | -H | |
| -CH₂-C₆H₃(OCH₃)(OH) | -H | Structure confirmed by $^1$H-NMR data |
| -CH₂-C₆H₄-CF₃ (p) | -H | |
| -CH₂-C₆H₄-OCF₃ (p) | -H | |
| -CH₂-C₆H₄-SCF₃ (p) | -H | |
| -CH₂-C₆H₄-N(CH₃)₂ (p) | -H | |
| -CH₂-CH₂-(2-furyl) | -CH₂-CH₂-(2-furyl) | |
| -CH₂-CH₂-CH₂-C₆H₅ | -CH₂-CH₂-CH₂-C₆H₅ | |
| -CH₂-CH=CH-C₆H₅ | -H | |

TABLE 1-continued
N-alkylation of nikkomycin X with aldehydes and ketones

| $R_1$ | $R_2$ | Physical Data |
|---|---|---|
| -CH₂-(1-(2-hydroxynaphthyl)) | —H | Structure confirmed by ¹H-NMR data |

TABLE 2
Derivatisation of the formyl group of nikkomycin X

| R | Physical Data |
|---|---|
| H | Structure confirmed by ¹H-NMR data |
| —OH | |
| —NH—CH₃ | |
| —N(CH₃)₂ | |
| —NH—C(=O)—NH₂ | |
| —NH—C(=NH)—NH₂ | |
| —NH—C(=S)—NH₂ | |
| —NH—CH₂—CH₂—OH | |
| —NH—C₆H₅ | |

TABLE 2-continued
Derivatisation of the formyl group of nikkomycin X

| R | Physical Data |
|---|---|
| —NH—C₆H₄—Cl (para) | Structure confirmed by ¹H-NMR data |
| —NH—C₆H₄—COOH (para) | |
| —NH—(2-pyrimidinyl) | |

TABLE 3
Derivatisation of nikkomycin X with isocyanates

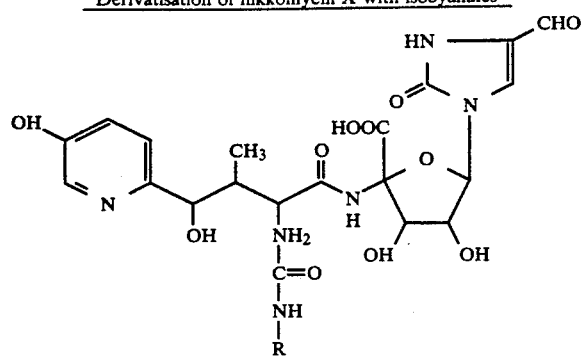

| R | Physical Data |
|---|---|
| —CH₃ | Structure confirmed by ¹H-NMR data |
| (phenyl) | |
| (3-chlorophenyl) | |
| (3-trifluoromethylphenyl) | |
| (4-methyl-2-chlorophenyl) | |
| —CH₂—(phenyl) | |

TABLE 4
N-acylation of nikkomycin X with α-amino acid reactive esters

| R | Configuration of α-NH₂ | Physical data |
|---|---|---|
| —CH₃ | L | Structure confirmed by ¹H-NMR data |

TABLE 5
N-acylation of nikkomycin $C_x$ with α-amino acid reactive ester

| R | Configuration of α-NH₂ | Physical Data Structure confirmed by ¹H-NMR data |
|---|---|---|
| —H | L | |
| —CH₃ | L | |
| —CH(CH₃)₂ | L | |
| —CH₂—CH(CH₃)₂ | L | |
| —CH(CH₂—CH₃)(CH₃) | L | |
| —CH(CH₃)(OH) | L | |
| —CH₂—CH₂—S—CH₃ | L | |
| —CH₂—CH₂—S(O)—CH₃ | L | |
| —(CH₂)₃—NH₂ | L | |
| —(CH₂)₃—NH—C(O)—CH₃ | L | |
| —(CH₂)₃—NH—C(O)—NH₂ | L | |
| —(CH₂)₄—NH₂ | L | |
| —(CH₂)₄—NH—C(O)—CH₃ | L | |
| —CH₂—C(O)—NH₂ | L | |
| —(CH₂)₂—COOH | L | |

TABLE 5-continued
N-acylation of nikkomycin $C_x$ with α-amino acid reactive ester

| R | Configuration of α-NH$_2$ | Physical Data Structure confirmed by $^1$H-NMR data |
|---|---|---|
| —CH$_2$—C(=O)—O—CH$_2$—C$_6$H$_5$ | L | |
| —CH$_2$—C$_6$H$_5$ | L | |
| —CH$_2$—C$_6$H$_4$—OH | L | |
| —CH$_2$—C$_6$H$_4$—O—CH$_2$—C$_6$H$_5$ | L | |
| —CH$_2$—CH$_2$—C$_6$H$_5$ | L | |
| —CH$_2$—CH$_2$—C$_6$H$_5$ | D | |
| —CH$_2$—CH$_2$—C$_6$H$_5$ | D/L | |
| —CH$_2$—CH$_2$—C$_6$H$_4$—OH | D/L | |
| —CH$_2$—CH$_2$—C$_6$H$_4$—OCH$_3$ | D/L | |
| —CH$_2$—C(=O)—C$_6$H$_5$ | D/L | |
| —CH$_2$—O—C$_6$H$_5$ | D/L | |
| —CH$_2$—O—C$_6$H$_4$—Cl | D/L | |
| —CH$_2$—O—CH$_2$—C$_6$H$_5$ | L | |
| —CH$_2$—(indole) | L | |

TABLE 6
N-acylation of nikkomycin $C_x$ with acid reactive esters

| R | Configuration of α-NH | Physical data |
|---|---|---|
| pyrrolidine (2-yl) | L | Structure confirmed by $^1$H-NMR data |
| —CH$_2$—NH—CH$_3$ | — | — |

TABLE 6-continued

N-acylation of nikkomycin $C_x$ with acid reactive esters

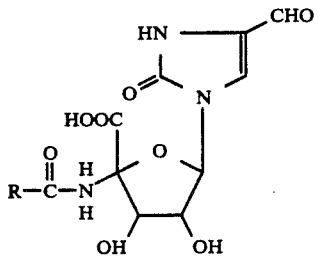

| R | Configuration of α-NH | Physical data |
|---|---|---|
| -CH(NHCH₃)-CH₂-C₆H₅ | L | |
| -C(=N-)(-CH₂-CH(O-)-C₆H₅) | — | |

TABLE 7

N-acylation of nikkomycin $C_z$ with α-amino acid reactive esters

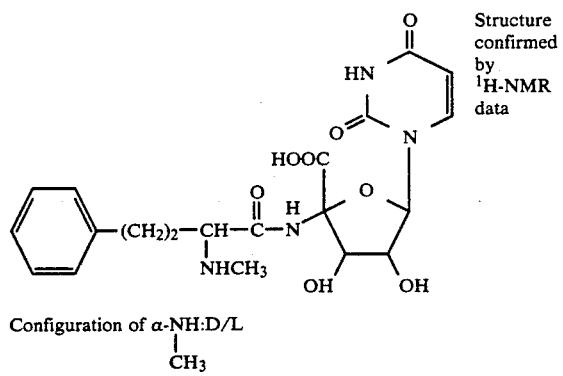

Configuration of α-NH:D/L
CH₃

Physical Data: Structure confirmed by ¹H-NMR data

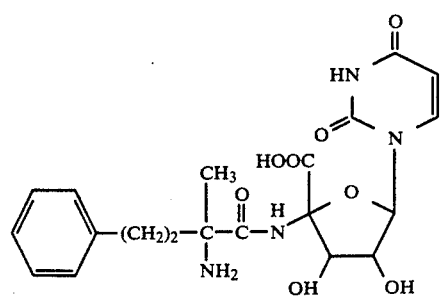

Configuration of α-NH₂:D/L

TABLE 7-continued

N-acylation of nikkomycin $C_z$ with α-amino acid reactive esters

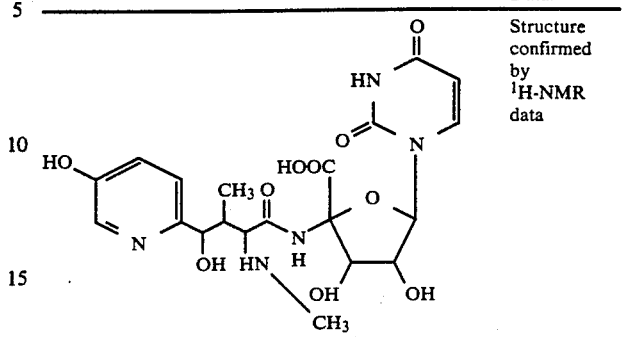

N-Methylnikkomycin Z

Physical Data: Structure confirmed by ¹H-NMR data

The compositions according to the invention can be used according to the invention and display antimicrobial actions, in particular powerful antimycotic actions. They possess a very broad antimycotic action spectrum, especially against dermatophytes and yeasts as well as biphasic fungi, for example against varieties of Candida, such as *Candida albicans*, varieties of Epidermophyton, such as *Epidermophyton floccosum*, varieties of Aspergillus, such as *Aspergillus niger* and *Aspergillus fumigatus*, varieties of Trichophyton, such as *Trichophyton mentagrophytes*, varieties of Microsporon, such as *Microsporon felineum* and varieties of Torulopsis, such as *Torulopsis glabrata*. The listing of these micro-organisms in no way implies a limitation of the germs which can be combated but is only of illustrative character. Such fungi include also *Coccidioides immitis*, *Histoplasma capsulatum*, *Blastomyces dermatitidis* and *Paracoccidioides brasiliensis*.

Examples which may be mentioned of fields of indication in human medicine are: dermatomycoses and systemic mycoses caused by *Trichophyton mentagrophytes* and other varieties of Trichophyton, varieties of Microsporon, *Epidermophyton floccosum*, yeasts and biphasic fungi as well as moulds and varieties of Candida.

Examples which may be mentioned of field of indication in veterinary medicine are: all dermatomycoses and systemic mycoses, especially those caused by the abovementioned pathogens.

The present invention includes pharmaceutical formulations which, in addition to non-toxic, inert pharmaceutically suitable excipients, contain one or more active compounds according to the invention, or which consist of one or more active compounds according to the invention, as well as processes for the preparation of these formulations.

The present invention also includes pharmaceutical formulations in dosage units. This means that the formulations are in the form of individual parts, for example tablets, dragees, capsules, pills, suppositories and ampoules, of which the content of active compound corresponds to a fraction or a multiple of an individual dose. The dosage units can contain, for example, 1, 2, 3 or 4 individual doses or ½, ⅓ or ¼ or an individual dose. An individual dose preferably contains the amount of active compound which is given in one administration and which usually corresponds to a whole, a half, a third or a quarter of a daily dose.

By non-toxic, inert pharmaceutically suitable excipients there are to be understood solid, semi-solid or liquid diluents, fillers and formulation auxiliaries of every kind.

Tablets, dragees, capsules, pills, granules, suppositories, solutions, suspensions and emulsions, pastes, ointments, gels, creams lotions, powders and sprays may be mentioned as preferred pharmaceutical formulations.

Tablets, dragees, capsules, pills and granules can contain the active compound or compounds alongside the customary excipients, such as (a) fillers and extenders, for example starches, lactose, sucrose, glucose, mannitol and silica, (b) binders, for example carboxymethylcellulose, alginates, gelatine and polvinylpyrrolidone, (c) humectants, for example glycerol, (d) disintegrating agents, for example agar-agar, calcium carbonate and sodium bicarbonate, (d) solution retarders, for example paraffin, and (f) resorption accelerators, for example cetyl alcohol and glycerol monostearate, (h) adsorbents, for example kaolin and bentonite, and (i) lubricants, for example talc, calcium stearate and magnesium stearate and solid polyethylene glycols, or mixtures of the substances listed under (a) to (i).

The tablets, dragees, capsules, pills and granules can be provided with the customary coatings and shells, optionally containing opacifying agents, and can also be of such composition that they release the active compound or compounds only, or preferentially, in a certain part of the intestinal tracts, optionally in a delayed manner, examples of embedding compositions which can be used being polymeric substances and waxes.

The active compound or compounds, optionally together with one or more of the abovementioned excipients can also be in a micro-encapsulated form.

Suppositories can contain, in addition to the active compound or compounds, the customary water-soluble or water-insoluble excipients, for example polyethylene glycols, fats, for example cacao fat, an higher esters (for example $C_{14}$-alcohol with $C_{16}$-fatty acid), or mixtures of these substances.

Ointments, pastes, creams and gels can contain, in addition to the active compound or compounds, the customary excipients, for example animal and vegetable fats, waxes, paraffins, starches, tragacanth, cellulose derivatives, polyethylene glycols, silicones, bentonites, silica, talc and zinc oxide, or mixtures of these substances.

Powders and sprays can contain, in addition to the active compound or compounds, the customary excipients, for example lactose, talc, silica, aluminium hydroxide, calcium silicate and polyamide powders or mixtures of these substances. Sprays can additionally contain the customary propellants, for example chlorofluorohydrocarbons.

Solutions and emulsions can contain, in addition to the active compound or compounds, the customary excipients, such as solvents, solubilising agents and emulsifiers, for example water, ethyl, alcohol, isopropyl alcohol, ethyl carbonate, ethyl acetate, benzyl alcohol, benzyl benzoate, propylene glycol, 1,3-butylene glycol, dimethylformamide, oils, especially cottonseed oil, groundnut oil, maize germ oil, olive oil, castor oil and sesame oil, glycerol-formal, tetrahydrofurfuryl alcohol, polyethylene glycols and fatty acid esters of sorbitane, or mixtures of these substances.

For parenteral administration, the solutions and emulsions can also be in a sterile form which is isotonic with blood.

Suspensions can contain, in addition to the active compound or compounds, the customary excipients, such as liquid diluents, for example water, ethyl alcohol or propylene glycol, suspending agents, for example ethoxylated isostearyl alcohols, polyoxyethylene sorbitol esters and sorbitane esters, micro-crystalline cellulose, aluminium metahydroxide, bentonite, agar-agar and tragacanth, or mixtures of these substances.

The formulation forms mentioned can also contain colorants, preservatives and additives which improve the odour and flavour, for example peppermint oil and eucalyptus oil, and sweeteners, for example saccharin.

The therapeutically active compounds should preferably be present in the abovementioned pharmaceutical formulations in a concentration of about 0.1 to 99.5, preferably of about 0.5 to 95,% by weight of the total mixture.

The abovementioned pharmaceutical formulations can also contain other pharmaceutical active compounds in addition to the active compounds according to the invention.

The abovementioned pharmaceutical formulations are prepared in the customary manner according to known methods, for example by mixing the active compound or compounds with the excipient or excipients.

The present invention also includes the use of the active compounds according to the invention, and of pharmaceutical formulations which contain one or more active compounds according to the invention, in human and veterinary medicine, for the prevention, alleviation and/or cure of the abovementioned diseases.

The active compounds or the pharmaceutical formulations can be administered locally, orally, parenterally, intraperitoneally and/or rectally, preferably parenterally, and in particular intravenously, and aerosilized In general, it has proved advantageous both in human medicine and in veterinary medicine, to administer the active compound or compounds according to the invention in total amounts of about 10 to 300, preferably 50 to 200, mg/kg of body weight every 24 hours, optionally in the form of several individual administrations, in order to achieve the desired results.

However, it can be necessary to deviate from the dosages mentioned, and in particular to do so as a function of the species and the body weight ofthe subject to be treated, the nature and severity of the disease, the nature of the formulation and of the administration of the medicament and the time or interval over which the administration takes place. Thus it can in some cases suffice to manage with less than the abovementioned amount of active compound, whilst in other cases the abovementioned amount of active compound must be exceeded. The particular optimum required and the type of administration of the active compounds can easily be determined by anyone skilled in the art on the basis of his expert knowledge.

The following experiments were performed to assess the spectrum of activity of the nikkomycin derivative known as Bay R 6966 which has the following structure:

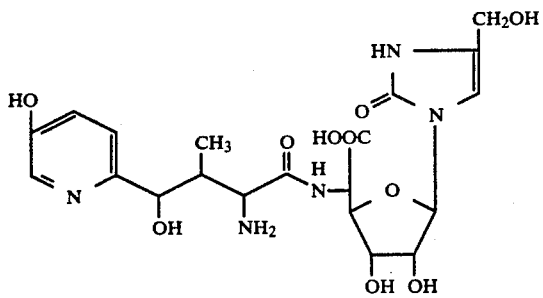

METHODS

IN VITRO TESTS

All test were performed using a microtiter format (96 well plates) employing either yeast nitrogen-base medium or Sabouraud's dextrose broth medium. The nikkomycin was dissolved directly in the medium, then diluted serially in the microtiter plates using 100 μl volumes. All fungal isolates were adjusted to a concentration of 20,000 cells/ml, then 100 μl of suspension was added to each duplicate well. All isolates were incubated at 30° C. with the exception of B. dermatitidis, which was incubated at 37° C. Plates were read at 48h except for B. dermatitidis, which was read at 96h. Plates were read visually with endpoints judged as the lowest concentration (expressed as ug/ml) showing no visible evidence of turbidity (growth).

IN VIVO TEST

A survival experiment was conducted using a murine model of pulmonary blastomycosis (FIG. 1). The yeast phase of the dimorphic, highly chitinous Blastomyces dermatitidis strain 1389 was injected intravenously into female Swiss-Webster mice at an infective dose of $4.9 \times 10^4$ cfu. After a 48h delay, therapy was begun, with groups of 10 mice receiving either the agar vehicle (control group), 5 mg/kg, 20 mg/kg, or 50 mg/kg Bay R 6966 delivered in a volume of 0.1 ml orally B.I.D.. Therapy was for 10 days, with animals then held for mortalities.

RESULTS AND DSICUSSION

Results of the MIC determinations (Table 1) indicate a wide range of susceptibility of medically important fungi to the nikkomycin derivative Bay R 6966. The dimorphic, highly chitinous fungus B. dermatitidis is the most susceptible, while two isolates of Candida differ greatly in their susceptibility. The highly chitinous but not-dimorphic fungi C. neoformans and A. fumioatus show a moderate to high degree of resistance to this substance.

TABLE 1

| MIC'S* FOR BAY R 6966 | |
|---|---|
| ISOLATE | MIC (ug/ml) |
| Candida albicans | 500 |
| Candida tropicalis | >8,000 |
| Cryptococcus neoformans | >500 |
| Blastomyces dermatitidis | 120 |
| Aspergillus fumigatus | >8,000 |

*MIC's read at 48 h except B. derm. at 96 h.

The survival experiment using a model of blastomycosis indicates that the highly chitinous dimorphic fungus is susceptible in vivo in a dose-dependent fashion, with good survival in animals treated at 50 mg/kg in animals infected with a highly lethal dose.

Taken together, the data indicate that nikkomycin derivatives of this class are effective against select fungi, particularly those of the highly-chitinous dimorphic class.

Given the above disclosure, it is thought that variations will occur to those skilled in the art. Accordingly, it is intended that the above exampler should be construed as illustrative only and that the scope of the invention disclosed should be limited only by the following claims.

We claim:

1. A method of treating a mammal infected with a dimorphic, highly chitinous fungi, the method comprising administering to the mammal therapeutically effective amounts of a nikkomycin derivative having the following structure:

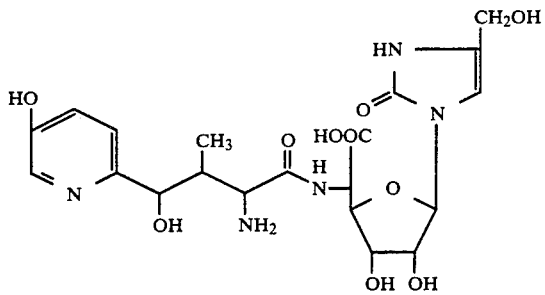

2. The method of claim 1 wherein the fungi have cell walls comprising at least about 10% by weight chitin.

3. The method of claim 2 wherein the cell walls comprise about 10-20% by weight chitin.

4. The method of claim 1 wherein the nikkomycin derivative is administered in a pharmaceutically acceptable vehicle.

5. The method of claim 4 wherein the nikkomycin derivative is administered orally.

6. The method of claim 1 wherein the fungi are selected from a group consisting of Coccidioides immitis, Histoplasma capsulatum, Blastomyces dermatitides, and Paracoccidioides brasiliensis.

7. The method of claim 1 wherein the fungi are Blastomyces dermatitides.

* * * * *